(12) United States Patent
Mumford (10) Patent No.: US 6,575,941 B1
(45) Date of Patent: Jun. 10, 2003

(54) PERMANENT LOCKING MECHANISM FOR SHARP-INSTRUMENT SAFETY GUARD

(75) Inventor: Yovette Mumford, Winchester, MA (US)

(73) Assignee: Safety Medical Supply International, Inc., Boston, MA (US)

( * ) Notice: Subject to any disclaimer, the term of this patent is extended or adjusted under 35 U.S.C. 154(b) by 0 days.

(21) Appl. No.: 09/436,741

(22) Filed: Nov. 9, 1999

Related U.S. Application Data (63) Continuation-in-part of application No. 09/220,499, filed on Dec. 24, 1998.
(60) Provisional application No. 60/119,373, filed on Feb. 9, 1999.

(51) Int. Cl.$^7$ ................................................ A61M 5/32
(52) U.S. Cl. ........................................................ 604/192
(58) Field of Search .............................. 604/192, 263, 604/264, 187, 188, 193, 194, 195, 196, 197, 198, 199

(56) References Cited

U.S. PATENT DOCUMENTS

| | | | |
|---|---|---|---|
| 3,658,061 A | 4/1972 | Hall | 128/214.4 |
| 4,664,259 A | 5/1987 | Landis | 206/365 |
| 4,820,277 A | 4/1989 | Norelli | 604/192 |
| 4,867,746 A | 9/1989 | Dufresne | 604/192 |
| 5,188,611 A | 2/1993 | Orgain | 604/192 |
| 5,509,907 A | * 4/1996 | Bevilacqua | 604/263 |
| 5,669,889 A | 9/1997 | Gyure et al. | 604/263 |
| 5,746,726 A | * 5/1998 | Sweeney et al. | 604/263 |
| 5,913,846 A | * 6/1999 | Szabo | 604/263 |

* cited by examiner

Primary Examiner—Anhtuan T. Nguyen
Assistant Examiner—Ann Y. Lam (57) ABSTRACT

A safety guard is described for use with sharp instruments, particularly with medical venipuncture instruments, and more particularly with hypodermic syringes. The safety guard uses a hinged single-piece assembly in which the safety guard is held in a locked position with a series of lugs formed as part of the base of the device and a series of tabs formed as part of the longitudinal member of the device. This arrangement makes the device especially resistant to the application of transverse or torsional forces. The longitudinal member further includes an opening lip that allows the guard to be opened easily without exposing the practitioner to the sharp end of the instrument. A permanent locking mechanism is provided so that the safety guard may be locked in place after use to prevent reuse of the instrument.

4 Claims, 8 Drawing Sheets

PERMANENT LOCKING MECHANISM FOR SHARP-INSTRUMENT SAFETY GUARD

RELATED APPLICATION

This application is a continuation-in-part application of application Ser. No. 09/220,499, filed Dec. 24, 1998, and claims the priority of Provisional Patent Application Serial No. 60/119,373, filed Feb. 9, 1999.

FIELD OF THE INVENTION

This invention relates to a device that protects against accidental contact with or puncture by sharp instruments. More particularly, it relates to an arrangement that protects against contact with and puncture by sharp medical instruments, such as, for example, hypodermic, blood-collection, and other needles.

BACKGROUND OF THE INVENTION

In recent years, there has been increasing concern among both health practitioners and the general public regarding the danger of transmission of toxic medications, microorganisms, and other dangerous pathogens through accidental puncture by sharp medical instruments, such as hypodermic and blood-collection needles. Modern medical techniques are often invasive and health practitioners routinely use a variety of venipuncture devices. Danger arises if a patient is injected with an instrument that has not been kept properly sterile, and it can also arise if there is accidental puncture of an individual by the instrument after it has been exposed to fluids such as infected blood.

In the past, a number of devices have been proposed that offer some level of protection to patients and health practitioners against such dangers. For any such device, there are several characteristics that should be achieved for the device to be considered successful. The design should be such that the safety device is convenient to use and minimizes the potential for inadvertent contact with the instrument both before and after use of the instrument. This is preferably achieved with a device that requires only a single hand to close the protective cover. The safety device should not interfere with use of the instrument itself, and the device should be both simple and convenient for the practitioner to use without danger that the practitioner will puncture himself or herself, and without danger that the practitioner will touch and contaminate the instrument. It is also desirable that it be possible for such a device to be made at low cost, especially when the devices are to be mass-produced.

Such protection devices have generally taken the form of some kind of safety guard that prevents contact with the sharp object when the instrument is not in use, and includes some mechanism by which the guard can be removed when the instrument is to be used. For such designs, the safety guard should be fastened to the instrument in a secure manner so that it is resistant to accidental breakage or dislodgement. It is also advantageous that there be a mechanism by which any excess fluid can discharge from the device after the safety guard is replaced. Other desirable characteristics are that the design of the device be such that it can be used with a variety of medical instruments and can be manufactured inexpensively.

U.S. Pat. No. 4,867,746 discloses a device having a safety portion connected to the instrument with a flexible body that obscures the view of the practitioner during operation of the instrument. This device is useful only for low-angle insertions into a patient's skin, because the protective portion of the device can only be moved as far as permitted by the flexibility of the body. Moreover, this device offers minimal, if any, protection against contamination of the instrument prior to its use. Further, there is a significant danger of accidental breakage of the safety device if the flexible body is displaced by too great an amount in an effort to use the instrument for a larger-angle insertion.

Danger of accidental breakage is also present in the device disclosed in U.S. Pat. No. 3,658,061, which comprises a slotted flexible plastic sleeve that snaps over the entire length of the instrument with a rotational action. The force required to lock the mechanism during this rotational operation may lead to accidental breakage. Moreover, the device appears unsuitable for adaptation to types of instruments other than hypodermic needles because of its characteristic shape.

U.S. Pat. No. 4,664,259 discloses a device having a cover attached to the device by a hinge, but the locking mechanism is configured so that some torque must be applied to the cover to release it. Because such protective covers are often constructed of polymeric material, a design that requires the application of torque is inherently inferior since a practitioner may inadvertently apply too great a torque to the small plastic device and break it. An alternative embodiment of the device disclosed in U.S. Pat. No. 4,664,259 involves a butterfly type of device wherein the cover is divided into two halves that separate individually. This is similar to the device presented in U.S. Pat. No. 4,820,277, which also uses a butterfly type of design. These designs do not permit easy single-handed replacement of the cover.

Figure 4:
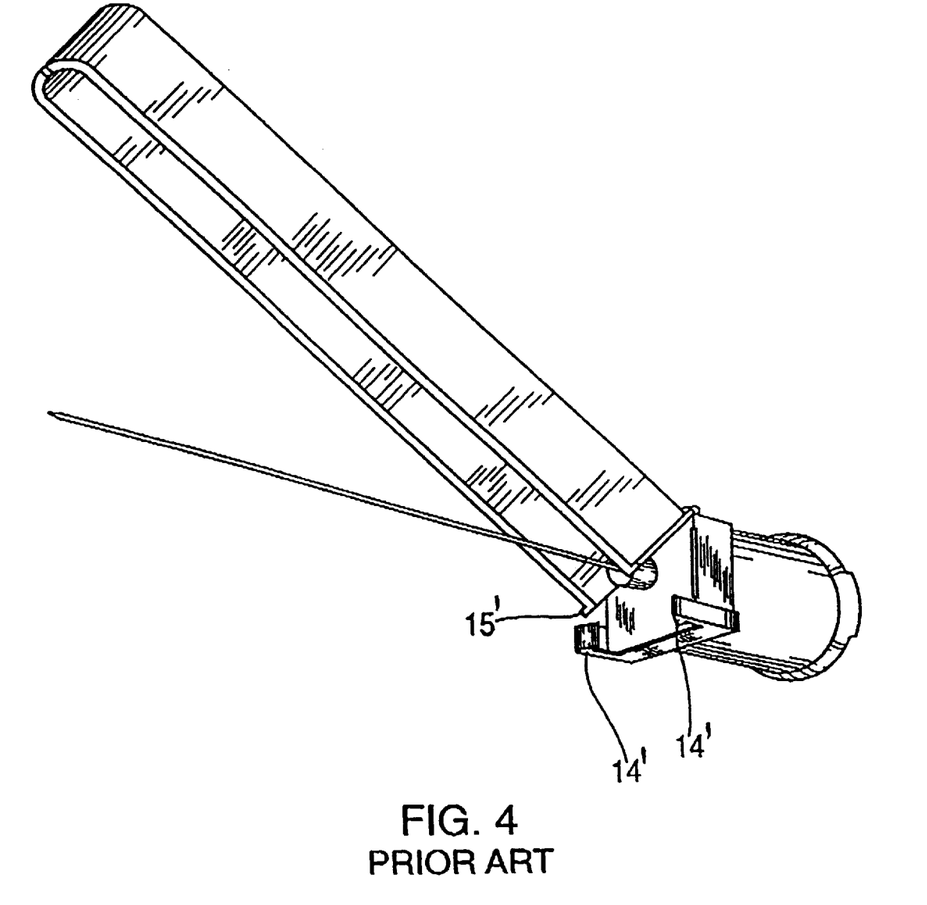
FIG. 4 is a perspective view of a known primary locking mechanism using plastic catches.

Another hinged device is disclosed in U.S. Pat. No. 5,188,611 ("the '611 patent"). In this design, the protective device comprises a slotted longitudinal member that swings over the sharp end of the instrument. This longitudinal member is attached to a collar with a flexible hinge; the collar engages the body of the instrument. The device may include two locking mechanisms. The primary locking mechanism consists of a partial sleeve in the longitudinal member that fits snugly over a hub. An alternative to this locking mechanism is shown in FIG. 4 of this application, wherein a pair of snap catches is used to hold the protective cover in place. The secondary locking mechanism comprises a keeper shelf that is positioned to block movement of the needle in the direction of the slot in the longitudinal member. This functions as a locking mechanism by prohibiting the needle from escaping the protective cover, but it will be readily appreciated that disengagement of this form of a locking device requires the application of either transverse or torsional forces on the protective device in order to release the instrument from the protective device. None of the different embodiments for the primary locking mechanism is designed specifically to resist the application of such torsional forces and the design is therefore susceptible to breakage.

Another disadvantage of the device described in the '611 patent and depicted in FIG. 4 is that, in preparing for making an injection, when the protective cover is opened by unlocking the protective cover from the snap catches to unshield the injection needle, accidental puncture may occur. Specifically, since the most convenient way to open the protective cover is to use one hand to hold the instrument and to use a finger of the other hand to push the top of the protective cover to swing it open. During this process, the sharp end of the needle is in proximity with and in the movement path of the finger pushing the protective cover to swing it open; this exposes the finger to a risk of accidental puncture. It is desirable that the risk of such accidental puncture be eliminated or reduced.

An additional device of the hinged type is described in U.S. Pat. No. 5,669,889 ("the '889 patent"). The device described there includes a permanent locking mechanism so that the protective cover cannot be removed after it is positioned over the sharp instrument. While the existence of a permanent locking mechanism ensures that the device cannot be reused after the protective cover has been positioned, there are numerous deficiencies with the design described there. Since the permanent locking mechanism is the only mechanism that can be used to hold the protective cover in place, the protective cover cannot be used to protect against puncture by the sharp instrument before it is used. Instead, it is necessary to include an additional separate protective sheath that covers the instrument before it is used. This additional protective sheath not only adds cost to the device but also requires separate disposal. Additionally, the existence of this sheath requires that the hinged protective cover be askew as shown in FIG. 1 of the '889 patent, making bulk packing inefficient.

The design described in the '889 patent also contemplates the use of two hands to close the protective cover. This is evident in the hinge design, which positions the protective cover when in use so that single-handed closure is awkward. As the patent describes, single-handed closure requires manipulation of the cover with the thumb. While a finger pad is provided to help ensure that the thumb is unlikely to touch the instrument despite its proximity to it, it would be preferable that the protective cover could be closed with a single-handed action that does not require fingers to be so close to the instrument. It will also be appreciated that where the instrument is a needle, there may be some splatter of fluid from the interior of the needle due to the action of closing the protective cover; if the fluid is contaminated blood, the danger to the practitioner is increased if one of his fingers needs to be near the device to close it.

Accordingly, it is desired that a safety guard be provided to protect against exposure to sharp instruments that does not interfere with operation of the instrument itself. It would similarly be beneficial to provide a design that is resistant to accidental breakage, including a secure locking mechanism that does not require the application of transverse or torsional forces, but is nonetheless resistant to such forces should they be applied by a user. The design should be intuitive to use and permit the guard to be removed without exposing the practitioner to a danger of accidental contact with the instrument. Also, it should be possible to replace the protective cover over the sharp end of the instrument after use with a single-handed motion that does not require the any of the practitioner's fingers to be near the instrument. The design should be such as to prevent the escape of any fluid splatter that results from closing the cover. Furthermore, there is a need to include a permanent locking mechanism that does not prevent the device from being shipped in the closed position, so as to use the same protective cover to protect against contact with the instrument both before and after use of the instrument.

SUMMARY OF THE INVENTION

The present invention provides a safety guard that protects against contact with an instrument having a sharp end. The present invention uses a hinge-type configuration wherein a longitudinal member is hingedly attached to a base that is in turn attached to the instrument. The hinge-type configuration permits the longitudinal member to swing over the sharp end of the instrument through a longitudinal slot in the longitudinal member. Preferably, the longitudinal member includes an opening lip at its end, which functions as a support for a user to push open the safety guard. The position of the opening lip ensures that the user's fingers are not in a position where they are likely to come into accidental contact with the sharp end of the instrument when the guard is opened. To open the guard and expose the instrument for use, a practitioner merely pushes or pulls on the opening lip with a finger, and this action naturally transfers the force applied to operate the hinge-type connection between the base and the longitudinal member. After using the instrument, the guard can be replaced to its closed position with a single hand by using a table or other flat surface to exert a force in the opposite direction on the longitudinal member.

The present invention provides a very secure locking mechanism when the safety guard is in the closed position. In accordance with the present invention, there are three small lugs on the base of the device that serve to lock the longitudinal member in place. There is a protrusion at the lower end of the side-opening slot of the protective member that serves to increase the strength and rigidity of the safety guard. On both sides of this protrusion are small tabs that interlock completely with the small lugs on the base of the device. This enables the longitudinal member to be tightly and stably affixed to the base, so that the longitudinal member and base act as a single guard entity when the device is in the closed position. This mechanism acts as a secure lock that has sufficient support around the perimeter of the lock to resist transverse or torsional forces should they be applied. Preferably, two of the three lugs are side lugs shaped such that they function as a snap catch to lock onto the protrusion when the guard is closed.

In one embodiment, the longitudinal member and base are molded out of polymeric material, while the hinge portion that connects them is made of a thin strip of polymeric material. The guard is made to open and close freely by relying on the flexibility of the polymeric material, making it convenient to use. In another embodiment of the invention, the hinge that connects the base to the protective cover can be made especially strong by fabricating it from a microscopic plastic helix that is subsequently encased in polymeric material. This design adds sufficient strength to the hinge that the protective cover can be opened as many as fifty times without breakage.

Where the instrument is a venipuncture needle that is beveled to facilitate injection of the needle through the skin and blood-vessel walls of a patient, the bevel is preferably oriented so that any splatter that occurs from the canal of the needle when the protective cover is closed is directed into the protective cover. This minimizes the possibility that a practitioner will come into contact with the splattered fluid.

In order to maintain the proper orientation of the bevel, the needle is attached to a well that includes a plurality of wings, one of which can be marked during the manufacturing process to assist in achieving the desired orientation. The well is at least partially enclosed within the base, which is otherwise hollow. These wings extend from the side of the top portion of the well and are easily visible during the manufacturing process. Another element that is important in maintaining the proper orientation of the bevel is to have the well protrude through a top surface of the base. This assists the manufacturing process by making it easier to identify the preferred bevel orientation during that process.

There is also a possibility during the manufacturing process of partially clogging the canal of the needle with polymeric material that is used to fabricate the base of the protective cover. This is primarily a result of large pressures that are needed to mold the base during the manufacturing process, resulting in some of the polymeric material being inadvertently pushed into the canal. It will readily be appreciated that this partial clogging can have a significant adverse affect on the operation of the instrument. In accordance with the present invention, this problem is overcome by forming a hole in one face of the hollow base. By including such a hole in the base, there is increased air circulation during the manufacturing process and there is also a means by which some of the pressures used during fabrication are released. Including the hole permits the base to be fabricated without significant clogging of the canal.

In another embodiment, the present invention also includes a permanent locking mechanism. This permanent locking mechanism is fabricated as a plastic tab on an interior wall of the longitudinal member. Once the safety guard is closed and the permanent locking mechanism engaged, the tab prevents the safety guard from being reopened. In a preferred embodiment, the permanent locking mechanism uses two tabs that are offset from each other in a direction transverse to the longitudinal member.

The present invention is directed to a safety guard to protect against inadvertent contact with an instrument having a sharp end, comprising: a hollow base disposed on such instrument in advance of such sharp end, the base comprising at least one side lug, an opposing lug, and a side face, the side face including a hole; a longitudinal member comprising a hinge end and a cover end, the hinge end hingedly connected to the base, the longitudinal member including two side walls and being of sufficient length to cover such sharp end and having a longitudinal slot wider than such sharp end, the opposing lug being disposed and shaped to fit into the longitudinal slot when the safety guard is in a closed position, the longitudinal member further comprising a protrusion at the hinge end, the protrusion being of such shape to be held between the at least one side lug and the opposing lug when the safety guard is in a closed position; and a permanent locking mechanism comprising a rear locking tab attached to one of the side walls of the longitudinal member and a front locking tab attached to the other of the side walls of the longitudinal member, the front locking tab disposed between the rear locking tab and the longitudinal slot. It is preferred that the rear locking tab have a trapezoidal cross section and that the front locking tab have a trapezoidal cross section; preferably the front locking tab is offset from the rear locking tab in a direction transverse to the longitudinal slot; it is also preferable that the front locking tab and the rear locking tab overlap in the transverse direction. It is also preferred that the at least one side lug be shaped such that the at least one side lug functions as a snap catch to lock the protrusion in place when the safety guard is in a closed position. It is additionally preferred that the longitudinal member further comprise an opening lip disposed at the cover end. The safety guard also preferably comprises a hinge that connects the longitudinal member to the base, the hinge comprising a microscopic helical structure; it is preferable that the base be composed of a polymeric material, that the longitudinal member be composed of the polymeric material, and that the microscopic helical structure be sheathed in the polymeric material. It is further preferred that the instrument be attached ta a support from which a plurality of wings protrudes, at least a portion of the support being enclosed within the base; preferably, at least four equally spaced wings protrude from the support; it is also preferable that the base comprise a top surface through which the support protrudes. In the preferred embodiment, the instrument is a venipuncture.

The present invention is also directed to a safety guard to protect against inadvertent contact with a venipuncture needle having a sharp end, comprising: a base disposed on such venipuncture needle in advance of such sharp end, the base comprising at least one side lug and an opposing lug; a longitudinal member comprising a hinge end and a cover end, the hinge end hingedly connected to the base, the longitudinal member including two side walls and being of sufficient length to cover such sharp end and having a longitudinal slot wider than such sharp end, the opposing lug being disposed and shaped to fit into the longitudinal slot when the safety guard is in a closed position, the longitudinal member further comprising a protrusion at the hinge end, the protrusion being of such shape to be held between the at least one side lug and the opposing lug when the safety guard is in a closed position, the venipuncture needle having a bevel at its sharp end oriented to face more than 90° away from the longitudinal slot when the safety guard is in the closed position; and a permanent locking mechanism comprising a locking tab attached to the longitudinal member. Preferably, the locking tab has a trapezoidal cross section. It is also preferred that the at least one side lug be shaped such that the at least one side lug functions as a snap catch to lock the protrusion in place when the safety guard is in a closed position. It is preferable that the longitudinal member further comprise an opening lip disposed at the cover end. It is also preferable that the safety guard further comprise a hinge that connects the longitudinal member to the base, the hinge comprising a microscopic helical structure; preferably, the base is composed of a polymeric material, the longitudinal member is composed of the polymeric material, and the microscopic helical structure is sheathed in the polymeric material. It is further preferred that the base be hollow and further comprise a side face that contains a hole. Additionally, it is preferable that the base be hollow and that the venipuncture needle be attached to a well from which at least four equally spaced wings protrude, at least a portion of the well being enclosed within the base; the base preferably comprises a top surface through which the well protrudes. It is yet further preferred that the bevel be oriented to face substantially 180° away from the longitudinal slot when the safety guard is in the closed position. In different embodiments, the venipuncture needle is the needle of a hypodermic syringe or is a blood collection needle.

Furthermore, the present invention is directed to a permanent locking mechanism for a safety guard, wherein the safety guard comprises a longitudinal member that includes two side walls and a longitudinal slot, comprising: a rear locking tab attached to one of the side walls; and a front locking tab attached to the other of the side walls. It is preferred that the rear locking tab have a trapezoidal cross section and that the front locking tab have a trapezoidal cross section; the front locking tab is preferably offset from the rear locking tab in a direction transverse to the longitudinal slot; it is also preferable that the front locking tab and the rear locking tab overlap in the transverse direction.

In addition, the present invention is directed to a safety guard to protect against inadvertent contact with a venipuncture needle having a sharp end, comprising: a hollow base disposed on such venipuncture needle in advance of such sharp end, the base comprising at least one side lug, an opposing lug, a top surface, and a side face, the side face including a hole; a longitudinal member comprising a hinge end and a cover end, the hinge end hingedly connected to the base, the longitudinal member including two side walls and being of sufficient length to cover such sharp end and having a longitudinal slot wider than such sharp end, the opposing lug being disposed and shaped to fit into the longitudinal slot when the safety guard is in a closed position, the longitudinal member further comprising a protrusion at the hinge end, the protrusion being of such shape to be held between the at least one side lug and the opposing lug when the safety guard is in a closed position, the venipuncture needle having a bevel at its sharp end oriented to face more than 90° away from the longitudinal slot when the safety guard is in the closed position; a hinge that connects the longitudinal member to the base, the hinge comprising a microscopic helical structure; and a permanent locking mechanism comprising a rear locking tab with a trapezoidal cross section attached to one of the side walls of the longitudinal member and a front locking tab with a trapezoidal cross section attached to the other of the side walls of the longitudinal member, the front locking tab disposed between the rear locking tab and the longitudinal slot and offset from and overlapping the rear locking tab in a direction transverse to the longitudinal slot; the venipuncture needle being attached to a well from which at least four equally spaced wings protrude, with at least a portion of the well enclosed within the base and the well protruding though the top surface of the base. Preferably, the base is composed of a polymeric material, the longitudinal member is composed of the polymeric material, and the microscopic helical structure is sheathed in the polymeric material. It is also preferred that the bevel be oriented to face substantially 180° away from the longitudinal slot when the safety guard is in the closed position. It is additionally preferred that the at least one side lug be shaped such that the at least one side lug functions as a snap catch to lock the protrusion in place when the safety guard is in a closed position. In different embodiments, the venipuncture needle is the needle of a hypodermic syringe or is a blood collection needle.

Also, the present invention is directed to a safety guard to protect against inadvertent contact with an instrument having a sharp end, comprising: a hollow base disposed on such instrument in advance of such sharp end, the base comprising at least one side lug, an opposing lug, and a side face, the side face including a hole; a longitudinal member comprising a hinge end and a cover end, the hinge end hingedly connected to the base, the longitudinal member being of sufficient length to cover such sharp end and having a longitudinal slot wider than such sharp end, the opposing lug being disposed and shaped to fit into the longitudinal slot when the safety guard is in a closed position, the longitudinal member further comprising a protrusion at the hinge end, the protrusion being of such shape to be held between the at least one side lug and the opposing lug when the safety guard is in a closed position; and a permanent locking mechanism comprising a locking tab attached to the interior of the longitudinal member. Preferably, the longitudinal member further comprises an opening lip disposed at the cover end. It is also preferred that the safety guard further comprise a hinge that connects the longitudinal member to the base, the hinge comprising a microscopic helical structure. It is further preferred that the at least one side lug be shaped such that the at least one side lug functions as a snap catch to lock the protrusion in place when the safety guard is in a closed position; preferably the base is composed of a polymeric material, the longitudinal member is composed of the polymeric material, and the microscopic helical structure is sheathed in the polymeric material. It is additionally preferred that the instrument be attached to a support from which a plurality of wings protrudes, at least a portion of the support being enclosed within the base; preferably, at least four equally spaced wings protrude from the support; it is also preferred that the base comprise a top surface through which the support protrudes. In the preferred embodiment, the instrument is a venipuncture needle.

Additionally, the present invention is directed to a method for protecting against contact with an instrument having a sharp end comprising providing a safety guard comprising: a base disposed on such venipuncture needle in advance of such sharp end, the base comprising at least one side lug and an opposing lug; a longitudinal member comprising a hinge end and a cover end, the hinge end hingedly connected to the base, the longitudinal member including two side walls and being of sufficient length to cover such sharp end and having a longitudinal slot wider than such sharp end, the opposing lug being disposed and shaped to fit into the longitudinal slot when the safety guard is in a closed position, the longitudinal member further comprising a protrusion at the hinge end, the protrusion being of such shape to be held between the at least one side lug and the opposing lug when the safety guard is in a closed position, the venipuncture needle having a bevel at its sharp end oriented to face more than 90° away from the longitudinal slot when the safety guard is in the closed position; and a permanent locking mechanism comprising a locking tab attached to the longitudinal member; and moving the longitudinal member into a position covering the sharp end.. It is preferred that the locking tab have a trapezoidal cross section. It is further preferred that the at least one side lug be shaped such that the at least one side lug functions as a snap catch to lock the protrusion in place when the safety guard is in a closed position. It is also preferred that the longitudinal member further comprise an opening lip disposed at the cover end. It is additionally preferred that the safety guard further comprise a hinge that connects the longitudinal member to the base, the hinge comprising a microscopic helical structure. Preferably, the base is hollow and further comprises a side face that contains a hole. It is yet further preferred that the base be hollow and that the venipuncture needle be attached to a well from which at least four equally spaced wings protrude, at least a portion of the well being enclosed within the base. It is also preferred that the bevel be oriented to face substantially 180° away from the longitudinal slot when the safety guard is in the closed position.

BRIEF DESCRIPTION OF THE DRAWINGS

The present invention will be understood more readily from the following detailed description of the preferred embodiments, when taken in conjunction with the accompanying drawings, in which.

DETAILED DESCRIPTION OF THE PREFERRED EMBODIMENTS

Figure 1A:
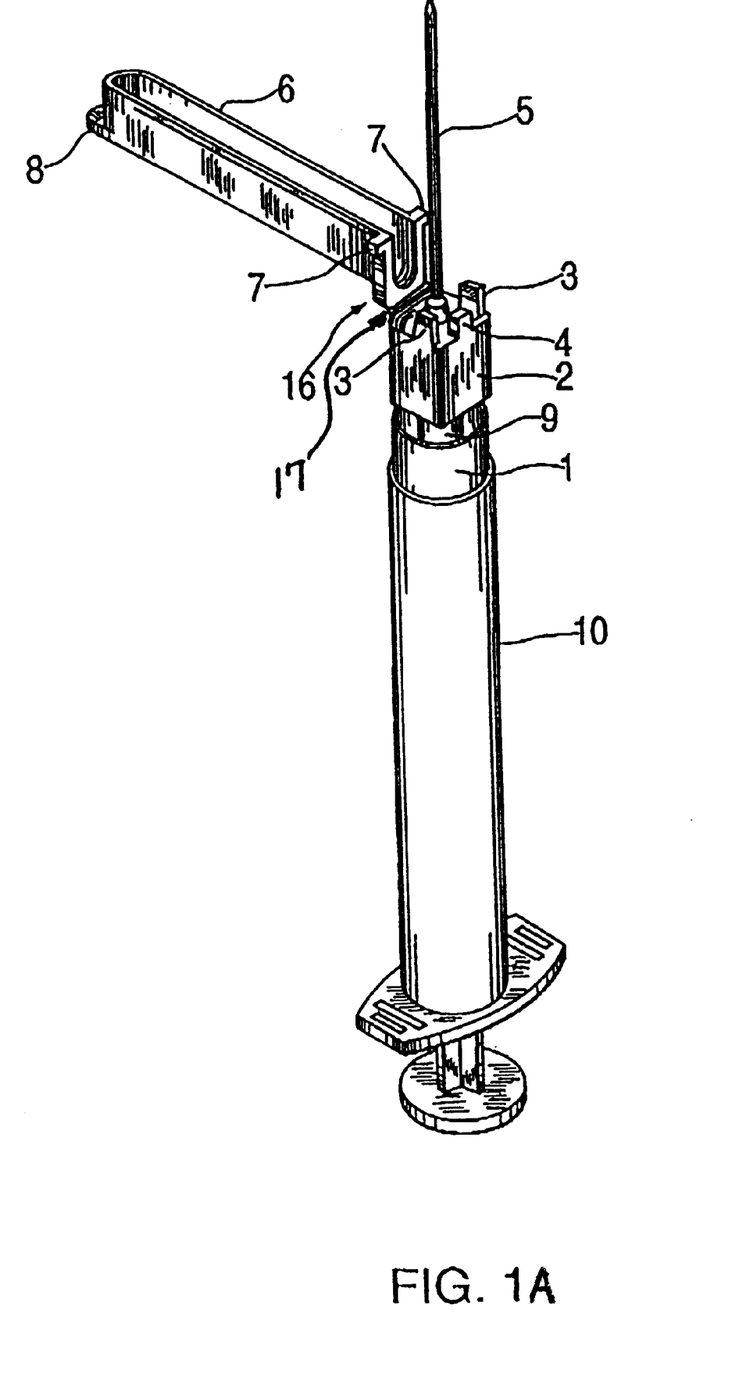
FIG. 1A is a perspective view of the device of the present invention as applied to a hypodermic needle.
Figure 1B:
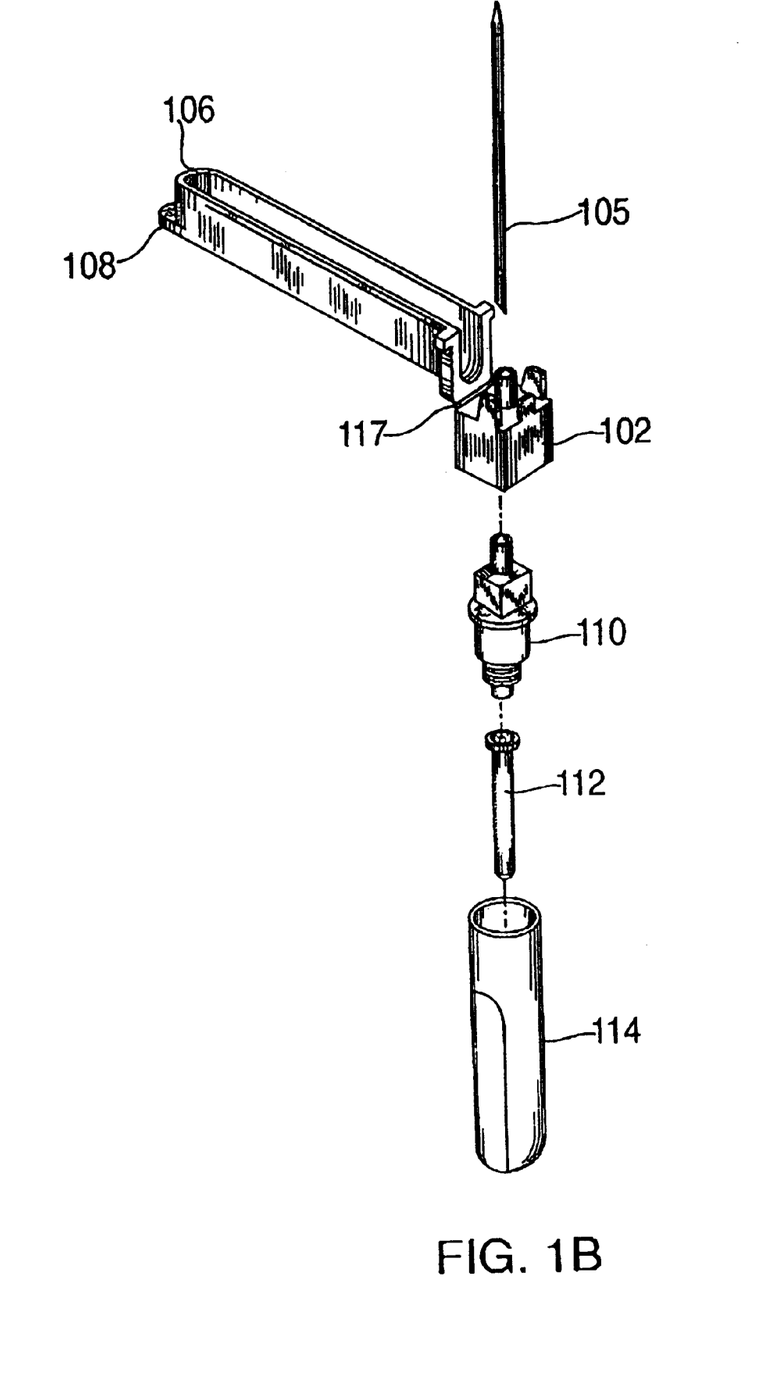
FIG. 1B is an exploded perspective view of the device of the present invention as applied to a blood-collection needle.

FIG. 1A shows a perspective view of a preferred embodiment of the present invention, where the sharp instrument is a hypodermic needle. As heretofore noted, this preferred embodiment of the invention is exemplary, and the invention may be configured for protection from a number of different sharp instruments, including a variety of medical instruments. For example, a blood-collection needle is shown in FIG. 1B, where the safety guard can be positioned over the needle generally as for the hypodermic needle. For convenience, this detailed description will be focused on the designs as illustrated for hypodermic and blood-collection needles, although it will be readily apparent to one skilled in the art that the invention may be also be used for other sharp instruments.

As shown in FIG. 1A, the safety guard comprises a longitudinal member 6 with a longitudinal slot that can cover a needle 5. The longitudinal member has a hinge end and a cover end, and as shown in FIG. 1A, the cover end of the longitudinal member 6 has an opening lip 8. At the hinge end, the longitudinal member 6 is attached to a base 2 with a hinge connection 17. Preferably, the longitudinal member 6, the base 2, and the hinge connection 17 are fabricated as a single continuous piece from molded polymeric material. Alternatively, these structures can be formed of metallic material. When the longitudinal member 6 is in a closed position to shield the needle 5, the opening lip 8 may be used to open the longitudinal member 6 by exerting a force in the direction that opens the hinge connection 17. It will be readily apparent that the opening lip 8 is important for ensuring that a practitioner's finger is not in close proximity with the needle 5, thereby minimizing the risk that the practitioner will inadvertently come into contact with the needle 5 while opening the longitudinal member 6.

The use of the safety guard on a blood-collection needle is shown in FIG. 1B. As generally for the hypodermic needle, a hinge end of a longitudinal member 106 is attached to a base 102 with a hinge connection 117. The longitudinal member 106, the base 102, and the hinge connection 117 are preferably fabricated as a single continuous piece from molded polymeric material. Alternatively, these structures can be formed of metallic material. The longitudinal member 106 includes an opening lip 108 at a cover end to facilitate opening the safety guard. When used with a blood-collection needle, a cannula 105 is attached to the base 102, which is attached to a needle seat 110. The needle seat 110 is further attached to a collection needle that is enclosed within a rubber cover 112. Blood is drawn from a patient through the cannula 105 and collected into a test tube through the collection needle. A protective lower cover 114 may be placed around the rubber cover 112 to protect against puncture with the collection needle.

Figure 2:
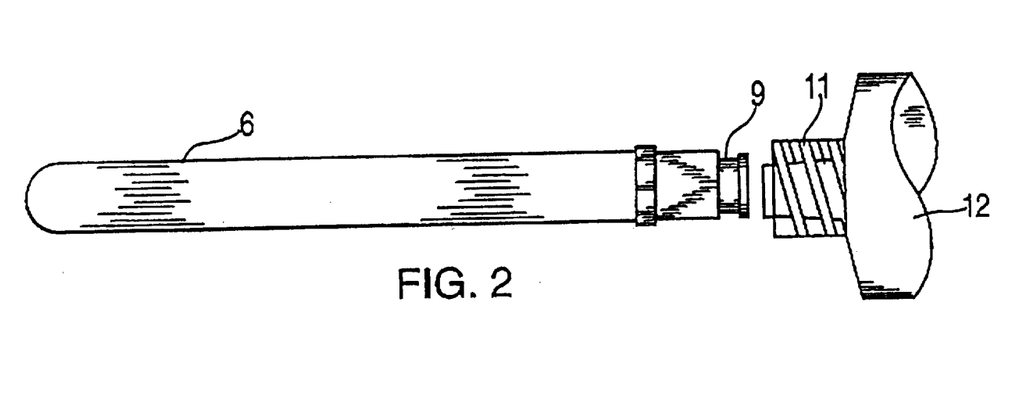
FIG. 2 is a side view of the device of the present invention showing how the device can be attached to an instrument such as a hypodermic syringe.

The configuration of the base 2 and how it may be connected to a hypodermic syringe 10 is more readily apparent from FIG. 2, which shows the a side view of the guard in a closed position. As illustrated, in this embodiment, the base 2 terminates in a set of luer tabs 9 which thread into a threaded luer 11 that is connected to the hypodermic syringe 10.

When the longitudinal member 6 is in the closed position, it is held secure by a locking mechanism of the present invention. It is most convenient to describe the locking mechanism by reference to FIG. 1A, with the guard in the open position, because the elements of the locking mechanism are more readily visible. The base 2 of the device includes two side structural protrusions or lugs 3 and one opposing structural protrusion or lug 4. The opposing lug 4 is positioned opposite the hinge connection 17 such that the opposing lug 4 will fit snugly into the side opening of the longitudinal member 6. The side lugs 3 are positioned on the two sides of the base 2. The longitudinal member 6 includes a protrusion 16, which is preferably horseshoe-shaped, at the hinge end of the longitudinal member 6. Preferably, on both sides of the protrusion 16 are small tabs 7 that are fabricated to fit snugly in the two gaps defined by each of the side lugs 3 with the opposing lug 4. More preferably, as illustrated in FIG. 1A, the side lugs 3 are shaped such that they also function as a pair of snap catches catching the protrusion 16 to hold the longitudinal member 6 in place when the safety guard is in the closed position. It will be appreciated that when the safety guard is in the closed position, the longitudinal member 6 is thus held very securely to the base 2 by the interlocking of the small tabs 7 with the side lugs 3 and the opposing lug 4. This configuration is given greater strength and the locking mechanism held even more securely as a result of the opposing lug 4 being held snugly in the longitudinal slot of the longitudinal member 6. In an alternative embodiment, the base can include only one side structural protrusion or lug 3 while the protrusion 16 can have one small tab 7 that can be interlocked with the side lug 3 and opposing lug 4. In another alternative embodiment, the tab 7 can be interlocked in a groove formed in the base 2 such as the groove obtained between one of the side lugs 3 and opposing lug 4 shown in FIG. 1A.

Figure 3:
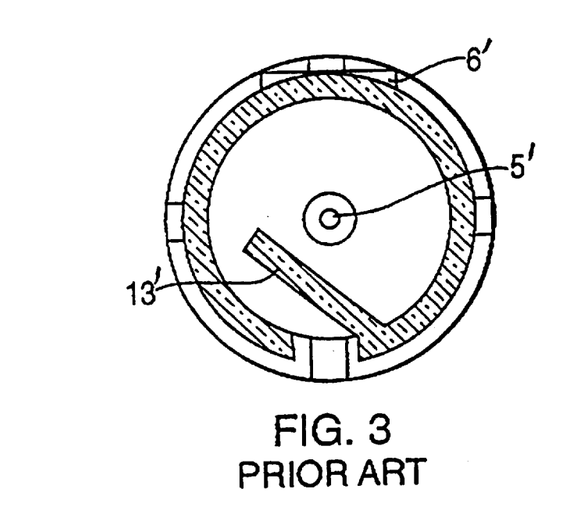
FIG. 3 is a view of a known secondary locking mechanism described as a keeper shelf.

This locking mechanism may be compared with some known protective devices as shown in FIGS. 3 and 4. In FIG. 3, a cross sectional view of the longitudinal member 6' is shown with a keeper shelf 13', which acts as a secondary locking mechanism. Keeper shelf 13' is positioned so that it is interposed between the opening in longitudinal member 6' and a needle 5'. In order to unlock the device, it is necessary either to rotate the longitudinal member 6' with a torsional force or to cause the longitudinal member 6' to move transversely with the application of a transverse force so that needle 5' may move out through the opening. It will be appreciated that this torsional or transverse force applied to longitudinal member 6' causes stress to a hinge connection between the base and the longitudinal member that may lead to accidental breakage of the device. This complexity is avoided in the present invention and unnecessary stress on the joint is eliminated.

It will further be appreciated that the present invention provides greater support than previously known devices to the joint between the base 2 and the longitudinal member 6 as a result of the improved locking mechanism. In the prior-art device illustrated in FIG. 4, for example, one can readily see that the primary locking mechanism is particularly susceptible to accidental breakage or undesired opening when the guard is subjected to transverse or torsional forces. Such a configuration is susceptible to accidental breakage or undesired opening as a result of transverse stresses placed on the joint between the longitudinal member and the base. In contradistinction, the present invention uses a series of lugs and tabs to provide a more secure lock that is resistant to such transverse stresses.

Figure 5:
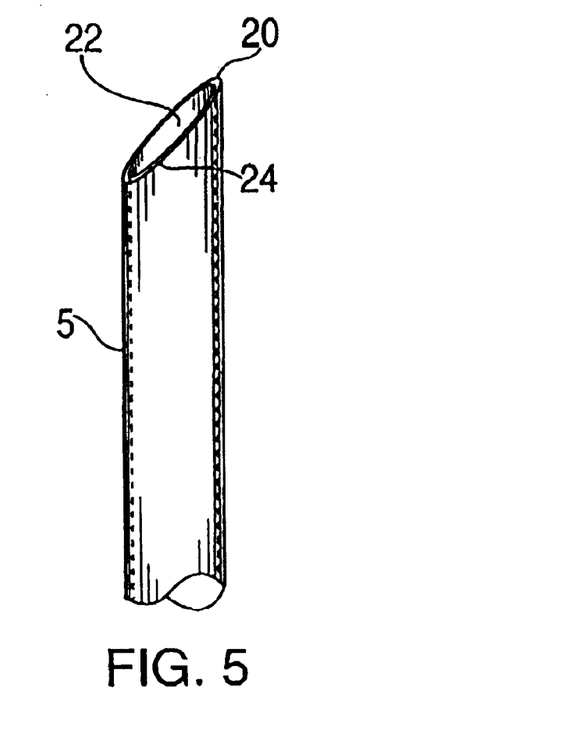
FIG. 5 is a perspective view of a venipuncture needle showing how the needle is fabricated with a beveled edge.

In embodiments of the invention where the sharp instrument is a venipuncture needle, there are a number of additional improvements within the scope of the present invention. FIG. 5 shows a perspective view of a venipuncture needle 5, which is a hollow cylinder formed of thin metal so that fluid can flow through the canal 22 of the needle 5. In order for the needle 5 to pierce the skin and blood-vessel walls of a patiently easily, the sharp end of the needle 5 comes to a point 20. This point is achieved by having the sharp end of the needle formed with a bevel 24.

Figure 6:
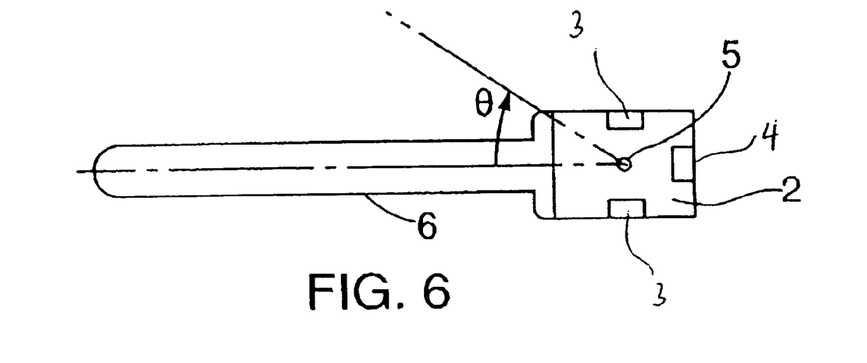
FIG. 6 is a top view of the device of the present invention as applied to a beveled venipuncture needle showing the angle at which the beveled edge of the needle is oriented.

The danger of contact with fluids from the venipuncture needle can be minimized by a suitable orientation of the bevel 24 of the needle 5 with the longitudinal member 6. The orientation of the bevel 24 can be defined by reference to FIG. 6. In this figure, a top view shows the needle 5 and the longitudinal member 6. The orientation of the bevel is defined by the angle θ, which is measured from the direction from the needle 5 towards the longitudinal axis of the longitudinal member 6. After the needle 5 has been used on a patient, there may be some residual fluid remaining in the canal 22 of the needle 5, which may be expelled or splattered from the needle 5 as a result of the snapping action of closing the longitudinal member 6. The danger of contact with any fluid that may be expelled or splattered during closure of the longitudinal member 6 after use may be minimized if $|\theta|<90°$, i.e. more than 90° away from the longitudinal slot of the longitudinal member 6. When the bevel 24 is so oriented, any fluid that is expelled or splattered during closure of the longitudinal member 6 will be caught by the longitudinal member 6, thereby preventing contact with the fluid by the practitioner. In an especially preferred embodiment of the invention, θ=0°, i.e. substantially 180° away from the longitudinal slot of the longitudinal member 6.

Figure 7:
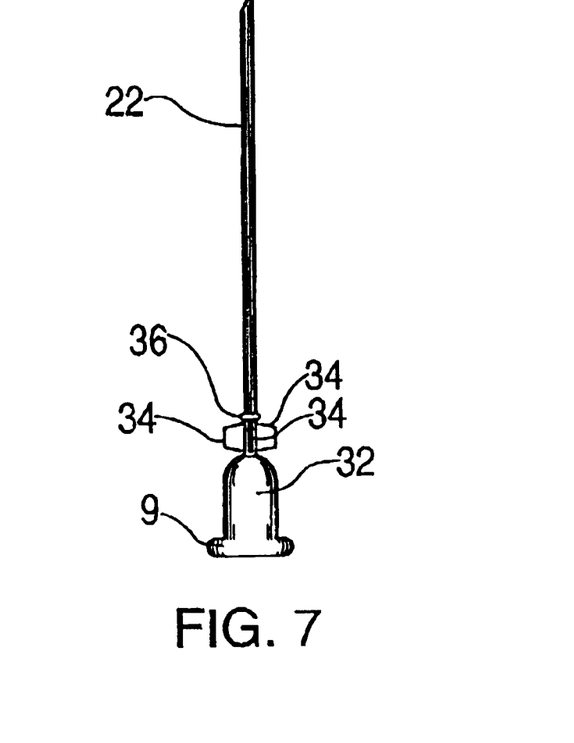
FIG. 7 is a side view of the present invention as applied to a beveled venipuncture needle showing a well attached to the needle, with wings attached to the well to facilitate achieving the proper orientation for the beveled edge of the needle.

The invention not only encompasses the structure of the apparatus but also the process by which the apparatus is manufactured, that permits the bevel 24 to be preferably oriented. FIG. 7 shows a side view of the needle 5 attached to luer tabs 9. The base 2 of the safety guard is omitted for ease of illustration. The needle 5 is connected to a well 32. The well 32 is constructed so that it is wide at the bottom, to accommodate the insertion of the structure with the luer tabs 9 into the syringe 10, and narrow at the top, to accommodate the connection with the needle 5. Affixed externally to the narrow top portion of the well 32 are a plurality of equally spaced wings 34. In a preferred embodiment of the invention there are four wings, separated from each other by 90°. When the safety guard is assembled, the well 32 is at least partially enclosed within the base 2, which is hollow. A similar structure can be used with other types of sharp instruments, with the luer tabs being replaced by the appropriate connection structure. For example, where the sharp instrument is a blood-collection needle, the wing structure is positioned on the needle seat 110.

During the manufacturing process, the needle 5 is connected with the well 32. The wing 34 that most closely defines the direction of the bevel 24 is marked, such as with a distinctive color. The wing that is marked is that wing that makes the smallest angle when compared with the direction of the bevel. Subsequently in the manufacturing process, the longitudinal member 6 is installed such that the longitudinal axis of the longitudinal member 6 is in the direction of the marked wing when the safety guard is in an open position. The bevel 24 will be oriented such that $|\theta|<90°$ whenever the number of wings 34 is greater than or equal to 4. In a preferred embodiment of the invention, the top portion of the well 32 protrudes from a top surface of the base 2 when the base 2 is installed. This protrusion of the well further facilitates achieving the desired orientation of the bevel 24.

Figure 8:
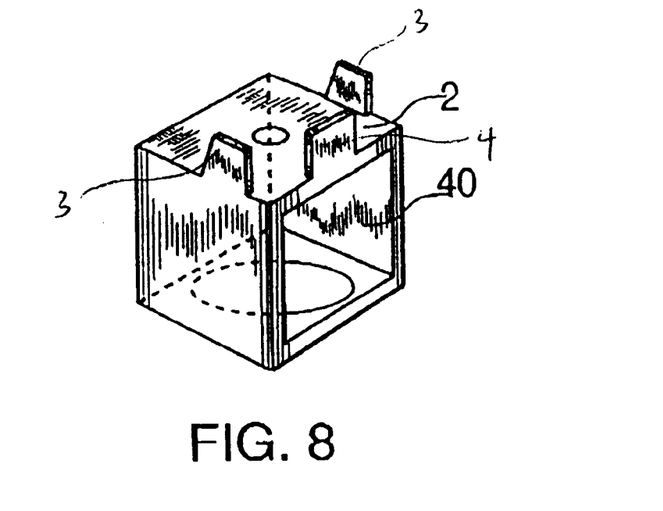
FIG. 8 is a perspective view an embodiment of the present invention in which the base of the safety guard is hollow and includes a hole in one of its side faces.

During fabrication of the base 2, there may be partial clogging of the canal 22 of the needle 5. This occurs because the base 2 is fabricated from soft heated polymeric material, and the high pressures used to mold the polymeric material may force some of the polymeric material into the canal 22. This clogging can be overcome by fabricating the base 2 to include a hole 40 as shown in FIG. 8, which shows a perspective view of the base 2. The base is fabricated of polymeric material so that the interior of the base is hollow; it is into this hollow interior that the well 32 is inserted. The base 2 is shown in FIG. 8 as a square cylinder, although the invention encompasses other shapes that may also be used for the base 2.

When the base 2 is fabricated with the hole 40, there is an increase in air circulation during the manufacturing process. The hole 40 also acts during the manufacturing process to relieve pressure that otherwise builds up in the interior of the base 2 during fabrication. This combination of reduced pressure and increased air circulation during the manufacturing process permits the base 2 to be formed while minimizing the possibility that the canal 22 of the needle 5 will become partially clogged. This clogging of the canal 22 can adversely affect the operation of the venipuncture device by making it difficult for fluids to flow easily through the canal. As a result of the inclusion of the hole 40, the overall usefulness of the device is enhanced. Additionally, the existence of the hole reduces the amount of polymeric material needed to fabricate the device without hampering the effectiveness of the locking mechanism produced by the tabs and lugs.

Figure 9:
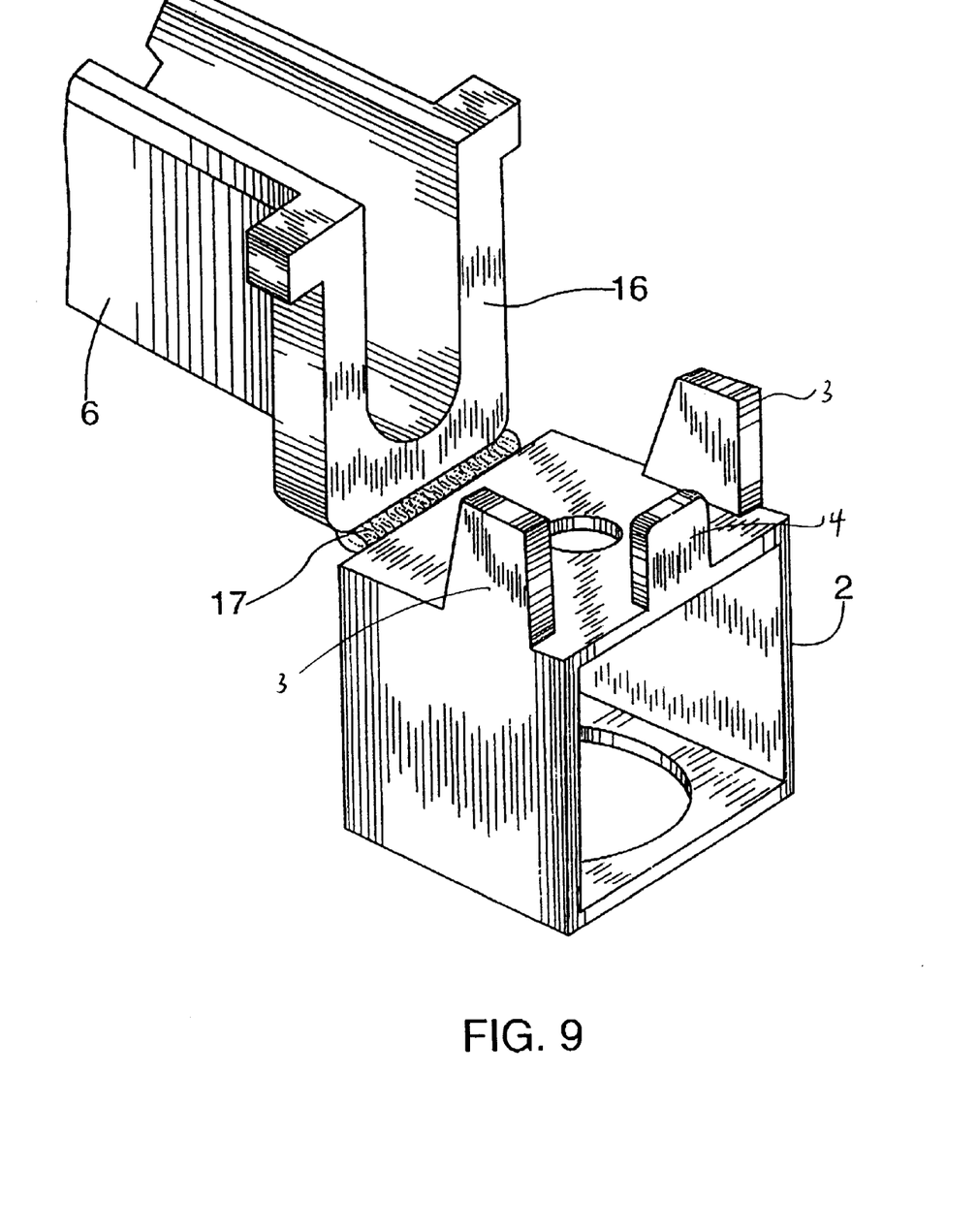
FIG. 9 is a perspective view of one embodiment of the present invention showing a detail of the hinge that connects the protective cover to the base.

The hinge connection 17 is fabricated so that it is integrated as a unit with the base 2 and the longitudinal member 6, and in one embodiment can be preferably made particularly strong by using the design shown in FIG. 9. The strength of the hinge connection 17 is directly related to the security of the connection between the longitudinal member 6 and the base 2. If the hinge connection 17 is weak and breaks, then the longitudinal member 6 will become removed from the base 2 and the device will not function. This is a particular disadvantage with the design disclosed in U.S. Pat. No. 5,669,889, which requires that the device be shipped with the protective cover in the open position; because in that design the protective cover is held to the instrument only with the hinge, and is not fabricated as an integrated unit, there is a substantial risk that the protective cover will be dislodged from the instrument before use. FIG. 9 shows a perspective view of the hinge connection 17 that connects the longitudinal member 6 to the base 2. The hinge connection 17 can be fabricated as a microscopic plastic helix that is subsequently sheathed in polymeric material. The microscopic helix adds strength to the hinge connection 17 so that the hinge connection 17 can be opened and closed repeatedly without showing significant weakening. With this design, the safety guard can be opened and closed as many as fifty times without breaking. Since the hinge connection 17 is fabricated as an integrated unit with the base 2 and the longitudinal member 6, this strength ensures that the possibility inadvertent removal of the safety guard from the instrument is extremely remote.

Figure 10:
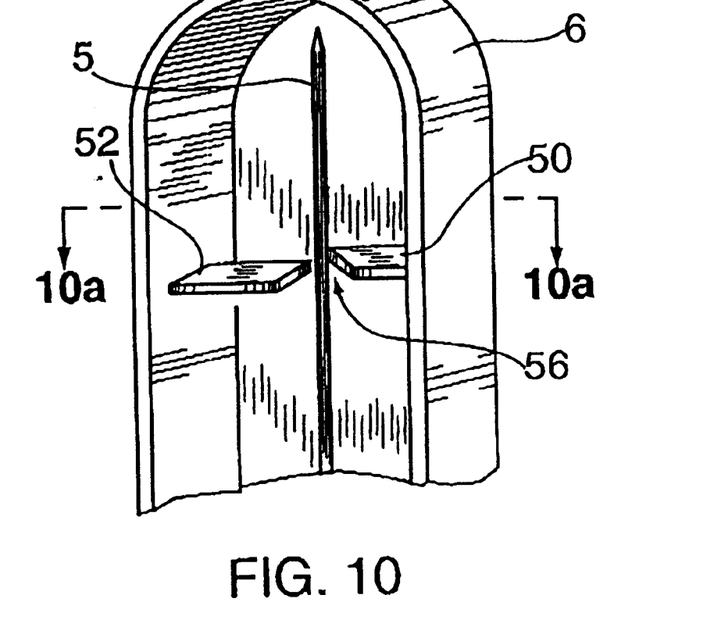
FIG. 10 is a perspective view of one embodiment of the present invention that includes a permanent locking mechanism.
Figure 10A:
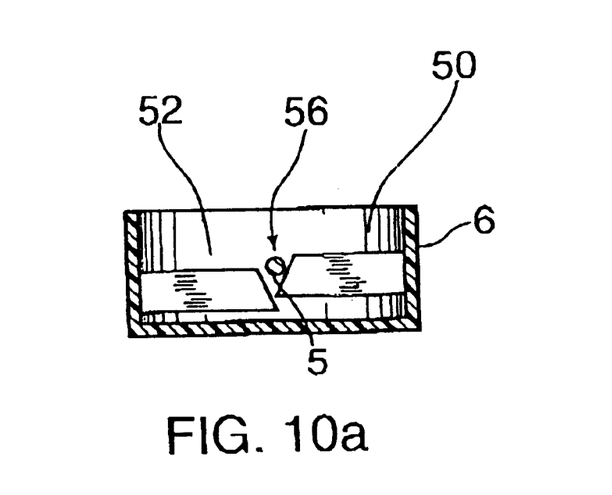

In one embodiment of the present invention, a permanent locking mechanism is included. The permanent locking mechanism is illustrated in FIG. 10. The locking mechanism may consist of a single locking tab but preferably consists of a rear locking tab 50 and a front locking tab 52. The rear locking tab 50 extends from an inner side of the longitudinal member 6 and the front locking tab 52 extends from the opposite inner side of the longitudinal member 6. Both the rear locking tab 50 and the front locking tab 52 are preferably shaped as trapezoidal prisms, having as their parallel edges the edges that are perpendicular to the sides of the longitudinal member 6 where they are attached. The longer side of the trapezoid is, for both the rear locking tab 50 and the front locking tab 52, at the edge opposite the longitudinal slot of the longitudinal member 6. The trapezoidal shape thus ensures that there is a region 56 in which the needle 5 can freely rest while the safety guard is closed without the permanent locking mechanism being engaged.

It is possible to lock the safety guard in its closed position with a single hand by using a table or other flat surface to exert a force on the longitudinal member 6. With a relatively small force, this action will move the protective cover over the needle 5 so that the needle 5 again rests in the open region 56. If a greater force is used, the needle will be pushed back behind both the rear locking tab 50 and the front locking tab 52, thereby locking the longitudinal member permanently in position. The permanent locking mechanism is more effective where there is an offset between the rear locking tab 50 and the front locking tab 52 in the direction transverse to the longitudinal member, and also some overlap between the rear locking tab 50 and the front locking tab 52 in the transverse direction. The use of this additional force makes it unlikely that the permanent locking mechanism will be engaged unintentionally. The existence of such a permanent locking mechanism does, however, permit a practitioner to lock the safety guard in position permanently after the instrument has been used. This not only prevents accidental contact with the instrument, but also prevents the instrument from being reused.

The following specific dimensions of a preferred embodiment of the present invention will make it clear how various components of the device are connected. In this preferred embodiment, the device is intended to be used with a venipuncture needle, such as a hypodermic or blood-collection needle, in which the needle has a length of 38 millimeters. The safety guard is fabricated of molded polymeric material. The longitudinal member 6 has a length of 44.5 millimeters, a width of 7.8 millimeters, and a thickness of 0.8 millimeters, with a longitudinal slot in its side that runs the full length of the longitudinal member 6. The base 2 has a square cylindrical shape with a height between 5.0 and 9.5 millimeters and a width of 7.8 millimeters. The two side lugs 3 and the opposing lug 4 each have a height of 3.0 millimeters and a width of 2.0 millimeters. The two small tabs 7 are on the sides of the horseshoe-shaped protrusion 16 and have a size that is identical to the size of the gap formed between the side lugs 3 and the opposing lug 4 on the base 2, so that they join together tightly. The opening lip 8 is formed at the upper end of the longitudinal member 6 with a semicircular shape with a radius of 3.9 millimeters.

In the above detailed description, the preferred embodiments are described only as illustrations but not as limitations. It will be readily apparent to one of skill in the art that these configurations can easily be adapted to other sharp implements.

As will be apparent to those skilled in the art, numerous modifications to the present invention may be made within the scope of the present invention, which is not intended to be limited except in accordance with the following claims.

What is claimed is:

1. A safety guard to protect against inadvertent contact with an instrument having a sharp end, comprising:
   a) a hollow base disposed on such instrument in advance of such sharp end, said base comprising at least one side lug, an opposing lug, and a side face, said face including a hole;
   b) a longitudinal member comprising a hinge end and a cover end, said hinge end hingedly connected to said base, said longitudinal member including two side walls and being of sufficient length to cover such sharp end and having a longitudinal slot wider than such sharp end, said opposing lug being disposed and shaped to fit into said longitudinal slot when said safety guard is in a closed position, said longitudinal member further comprising a protrusion at said hinge end, said protrusion being of such shape to be held between said at least one side lug and said opposing lug when said safety guard is in a closed position; and
   c) a permanent locking mechanism comprising a rear locking tab attached to one of said side walls of said longitudinal member and a front locking tab attached to the other of said side walls of said longitudinal member, said front locking tab disposed between said rear locking tab and said longitudinal slot
   d) wherein the rear locking tab has a trapezoidal cross section and wherein said front locking tab has a trapezoidal cross section and wherein the front locking tab is offset from said rear locking tab in a direction transverse to said longitudinal slot.

2. A safety guard to protect against inadvertent contact with an instrument having a sharp end, comprising:
   a) a hollow base disposed on such instrument in advance of such sharp end, said base comprising at least one side lug, an opposing lug, and a side face, said face including a hole;
   b) a longitudinal member comprising a hinge end and a cover end, said hinge end hingedly connected to said base, said longitudinal member including two side walls and being of sufficient length to cover such sharp end and having a longitudinal slot wider than such sharp end, said opposing lug being disposed and shaped to fit into said longitudinal slot when said safety guard is in a closed position, said longitudinal member further comprising a protusion at said hinge end, said profusion being of such shape to be held between said at least one side lug and said opposing lug when said safety guard is in a closed position; and
   c) a permanent locking mechanism comprising a rear locking tab attached to one of said side walls of said longitudinal member and a front locking tab attached to the other of said side walls of said longitudinal member, said front locking tab disposed between said rear locking tab and said longitudinal slot
   d) wherein the rear locking tab has a trapezoidal cross section and wherein said front locking tab has a trapezoidal cross section and said front locking tab is offset from said rear locking tab in a direction transverse to said longitudinal slot, and wherein said front locking tab and said rear locking tab overlap in said transverse direction.

3. A permanent locking mechanism for a safety guard, wherein said safety guard comprises a longitudinal member that includes two side walls and a longitudinal slot, comprising:
   a) a rear locking tab attached to one of said side walls; and a front locking tab attached to the other of said side walls b) wherein said rear-locking tab has a trapezoidal cross section and said front locking tab has a trapezoidal cross section
c) wherein said front locking tab is offset from said rear locking tab in a direction transverse to said longitudinal slot.

4. A permanent locking mechanism for a safety guard, wherein said safety guard comprises a longitudinal member that includes two side walls and a longitudinal slot, comprising:

rear locking tab attached to one of said side walls; and a front locking tab attached to the other of said side walls, wherein said rear-locking tab has a trapezoidal cross section and said front locking tab has a trapezoidal cross section, wherein said front locking tab is offset from said rear locking tab in a direction transverse to said longitudinal slot, wherein said front locking tab and said rear locking tab overlap in said transverse direction.

* * * * *